(12) United States Patent
Sedlov et al.

(10) Patent No.: US 11,844,366 B2
(45) Date of Patent: Dec. 19, 2023

(54) LYCOPENE COMPOSITION HAVING IMPROVED COLORANT PROPERTIES

(71) Applicant: LYCORED LTD., Beer-Sheva (IL)

(72) Inventors: Tanya Sedlov, Beer-Sheva (IL); Tatyana Atlasman, Beer-Sheva (IL); Morris Zelkha, Ramat-Gan (IL)

(73) Assignee: LYCORED LTD., Beer-Sheva (IL)

(*) Notice: Subject to any disclaimer, the term of this patent is extended or adjusted under 35 U.S.C. 154(b) by 0 days.

(21) Appl. No.: 15/536,444

(22) PCT Filed: Dec. 14, 2015

(86) PCT No.: PCT/IL2015/051212
§ 371 (c)(1),
(2) Date: Jun. 15, 2017

(87) PCT Pub. No.: WO2016/098106
PCT Pub. Date: Jun. 23, 2016

(65) Prior Publication Data
US 2018/0042276 A1     Feb. 15, 2018

Related U.S. Application Data

(60) Provisional application No. 62/092,431, filed on Dec. 16, 2014.

(51) Int. Cl.
| A23L 5/44 | (2016.01) |
| A23L 2/52 | (2006.01) |
| A23L 2/58 | (2006.01) |
| A23L 33/105 | (2016.01) |

(52) U.S. Cl.
CPC .................... *A23L 5/44* (2016.08); *A23L 2/52* (2013.01); *A23L 2/58* (2013.01); *A23L 33/105* (2016.08); *A23V 2002/00* (2013.01)

(58) Field of Classification Search
CPC . A23L 5/44; A23L 2/58; A23L 33/105; A23L 2/52; A23V 2002/00
See application file for complete search history.

(56) References Cited

U.S. PATENT DOCUMENTS

| 5,837,311 A | 11/1998 | Zelkha et al. | |
| 5,965,183 A * | 10/1999 | Hartal | A23L 5/44 426/250 |
| 6,235,315 B1 | 5/2001 | Runge et al. | |
| 2008/0207775 A1 * | 8/2008 | Musaeus | A61K 47/06 514/778 |
| 2010/0016597 A1 * | 1/2010 | Hirokawa | A61K 9/0019 546/152 |
| 2015/0004236 A1 * | 1/2015 | Sunil Kumar | A61K 31/01 424/489 |

FOREIGN PATENT DOCUMENTS

| CN | 1341686 A | 3/2002 |
| CN | 101297691 A1 | 11/2008 |
| CN | 102718619 A * | 10/2012 |
| EP | 0 608 027 | 7/1994 |
| JP | 2002193850 A | 7/2002 |
| JP | 2008/063476 A | 3/2008 |
| WO | WO03079816 A1 | 10/2003 |
| WO | WO 2004/016104 | 2/2004 |
| WO | WO2009/068432 A1 | 6/2009 |
| WO | WO2012/137209 A1 | 10/2012 |
| WO | WO 2013/041935 | 3/2013 |
| WO | WO-2013041935 A1 * | 3/2013 ............. A61K 31/01 |

OTHER PUBLICATIONS

Hunter, "Accuracy, Precision, and Stability of New Photo-electric Color Difference Meter", J Op Soc Am 38: 1094 (1948) (Year: 1948).*
Hunter, "Accuracy, Precision, and Stability of New Photo-electric Color Difference Meter", J Op Soc Am 48: 985 (1958) (Year: 1958).*
Dieter-Horn, Die Angewandte Makromolekulare Chemie, 166/167, pp. 139-153. (Year: 1989).*
International Search Report for PCT/IL2015/051212, dated Apr. 20, 2016, 4 pages.
Written Opinion of the ISA for PCT/IL2015/051212, dated Apr. 20, 2016, 5 pages.
"CIELAB color space" *Wikipedia*, last edited Sep. 11, 2018, 9 pages.
"ColorQuest® XE" User's Manual, HunterLab, Reston, VA, 161 pages (Mar. 2007).
Muratore et al. "Partial dehydration of cherry tomato at different temperature, and nutritional quality of the products" *Food Chemistry*, 111 (2008) 887-891.
Naviglio, D., et al., "Characterization of High Purity Lycopene from Tomato Wastes Using a New Pressurized Extraction Approach", J.Agric. Food Chem. 2008, 56, pp. 6227-6231.
Kendrick, A., "Natural food and beverage colourings", Editor(s): David Baines, Richard Seal, In Woodhead Publishing Series in Food Science, Technology and Nutrition, Natural Food Additives, Ingredients and Flavourings, Woodhead Publishing, 2012, p. 37.
Montesano, D., et al., "Innovative extraction procedure for obtaining high pure lycopene from tomato", Eur Food Res Technol (2008) p. 226:327-335.
Nishino, M., et al., "Photostability of Lycopene Dispersed in an Aqueous Solution", Biosci, Biotechnol. Biochem. (2011) 75(7), 1389-1391.

* cited by examiner

*Primary Examiner* — Abigail Vanhorn
(74) *Attorney, Agent, or Firm* — NIXON & VANDERHYE P.C.

(57) ABSTRACT

The present invention provides a tomato-derived composition comprising lycopene crystals at a concentration of at least 70% (w/w) and methylene chloride-insoluble material at a concentration of 10% (w/w) or less, wherein the size of said lycopene crystals is less than 1 micron. The present invention also encompasses a process for preparing said composition from tomato pulp.

15 Claims, No Drawings

LYCOPENE COMPOSITION HAVING IMPROVED COLORANT PROPERTIES

This application is the U.S. national phase of International Application No. PCT/IL2015/051212 filed 14 Dec. 2015, which designated the U.S. and claims the benefit of U.S. Provisional Application No. 62/092,431 filed 16 Dec. 2014, the entire contents of each of which are hereby incorporated by reference.

FIELD OF THE INVENTION

The present invention relates to a composition comprising a high concentration of lycopene crystals and a low concentration of insoluble material, said crystals having improved properties for use as a colorant, when compared with prior art preparations.

BACKGROUND OF THE INVENTION

Prior art publication U.S. Pat. No. 5,965,183 discloses and teaches a process for preparing stable lycopene concentrates. This process has been used successfully for several years to produce compositions containing about 70% (by weight) of crystalline lycopene, and said compositions have found commercial use in the food and beverage industry, in particular as natural, health-promoting food colorants.

There is, however, a long-felt need for a crystalline lycopene composition that has even better long-term stability and colorant properties.

The present invention fulfills this need.

SUMMARY OF THE INVENTION

The present invention is primarily directed to a composition comprising lycopene crystals at a concentration of greater than 70% (w/w), and methylene chloride-insoluble material at a concentration of less than 10%. Said composition has unexpectedly been found to possess far superior properties as a colorant material, when compared with prior art compositions. In particular, the crystals of the presently-disclosed composition are easier to grind to a size less than 1 micron, preferably in the range of 50-500 nm. In addition they are characterized by having improved color parameters (as measured, for example, using the L*a*b* color parameter system, as described in Hunter, R. S., December 1948, "Accuracy, Precision, and Stability of New Photo-electric Color-Difference Meter", JOSA 38(12): 1094.) Preferably, the color parameters of the presently-disclosed and claimed lycopene compositions are as follows:

a value: ≥25;
b value: 11.25-14.5;
b/a=0.45-0.55;
C value: 27.5-32.5;
h value: 24.2-27.0.

In one preferred embodiment of the composition, at least one of the color parameters has a value as defined above. In another preferred embodiment, all of said parameters have values as defined above.

Without wishing to be bound by theory, it is believed that both the enhanced grinding capability and the improved colorant properties are related, at least in part, to the reduced concentration of insoluble material in conjunction with the high lycopene concentration.

DETAILED DESCRIPTION OF PREFERRED EMBODIMENTS

The present inventors have now found that it is possible to prepare lycopene compositions, as defined hereinabove, having significantly reduced levels of methylene chloride-insoluble material (when compared to prior art compositions). This has been achieved by the use of tomato pulp having a much greater lycopene concentration than normally is found in this type of tomato material. By way of example, such lycopene-enriched tomato pulp may be produced by means of the process disclosed and taught in co-owned international patent application publication WO 2004/016104, the contents of which are incorporated herein in their entirety. The process taught in this document is capable of elevating the lycopene concentration in the pulp obtained thereby such that it is in the order of ×5 to ×15 greater than the lycopene concentration of the tomatoes from which said pulp was prepared. It is to be noted, however, that it is also possible to obtain lycopene-enriched tomato pulp preparations by other methods, said pulp preparations being used to produce the lycopene crystal composition of the present invention.

The present invention is thus also directed to a process for preparing a lycopene composition as defined hereinabove, wherein said process comprises the steps of separating pulp from crushed tomatoes, wherein said pulp has a lycopene concentration of at least 2000 ppm, extracting said pulp with a solvent to obtain an oleoresin, separating the lycopene crystals from the oleoresin, placing said lycopene crystals in a liquid medium that does not dissolve lycopene and grinding said crystals to an average particle size of less than 1 micron.

An exemplary process for preparing this composition is described in detail in Example 2, hereinbelow.

The present inventors have now surprisingly found that when lycopene crystals are isolated from pulp that was prepared in accordance with the teachings of WO 2004/016104, the level of insoluble material present in the lycopene composition is significantly reduced, when compared to compositions prepared using tomato pulp material that was prepared by other processes (e.g. as described in U.S. Pat. No. 5,837,311). Since tomato pulp produced by the process of WO 2004/016104 has not previously been used as a source material for preparing crystalline lycopene crystals, the results obtained by the present inventors concerning the low insoluble material concentrations in the composition of the present invention (see Example 5, hereinbelow) were entirely unexpected.

The 70% (or greater) lycopene composition of the present invention may be prepared from the aforementioned high-lycopene concentration pulp by means of any suitable method. In one preferred embodiment, however, the method described in co-owned U.S. Pat. No. 5,965,183 may be used. The contents of this publication are incorporated into the present disclosure in their entirety.

The present invention encompasses the above-mentioned composition comprising at least 70% lycopene and less than 10% methylene chloride-insoluble materials. In one preferred embodiment, said composition comprises less than 9% of such insoluble material. In another preferred embodiment, the composition comprises 7% or less insoluble material. In yet a further preferred embodiment, the composition comprises about 5% methylene-chloride insoluble material.

Generally, the lycopene crystals of the presently-claimed composition are contained within a medium which does not substantially dissolve lycopene. In one preferred embodiment, said medium is glycerol. In another preferred embodiment, said medium may be selected from the group consisting of propylene glycol, water, a lower alcohol such as ethanol, a water miscible liquid and a water soluble liquid.

In most preferred embodiments of the composition of the present invention, the size of the lycopene crystals will be in the range of 50-500 nm.

The present invention also encompasses the use of said composition to color foodstuffs, beverages, nutraceutical products or cosmetic products. The invention further includes said colored foodstuffs and beverages and nutraceutical or cosmetic products within its scope. The actual color or hue achieved when using the composition of the present invention to color or stain a food or beverage product will vary according to various different factors. However, generally the color achieved will be in the red range of the spectrum.

Example 1

Production of Lycopene Crystals Using a Prior Art Method (Comparative)

One ton of ripe tomatoes containing 165 ppm of lycopene (165 mg/kg) were washed and minced.

Tomato peels and seeds were separated from the crushed tomatoes through a sieve in two separate steps: in the first step a sieve of 8 mm was used, while a 2 mm sieve was employed for the second step.

After peel and seed removal, the resulting tomato juice was transferred into a vessel which was evacuated using negative pressure for 30 minutes. Then, the tomato juice was heated to 82-86° C. with a heat exchanger and separated into pulp (containing the tomato fibers and lycopene) and serum (containing soluble tomato solids) by passing it through a decanter. One ton of the tomato produced 70 kg of wet pulp, with an 80% moisture content and a lycopene concentration of 2000 ppm. The lycopene yield from this process was 95%.

The wet pulp was used as the raw material for the extraction of lycopene. Ethyl acetate was used as the solvent for the extraction, wherein the ratio between the ethyl acetate and the tomato pulp was 2.9:1 (w/w). The extraction was performed at a temperature of 60° C. for 4 hours.

The extraction process resulted in about 1.25 kg of tomato oleoresin. Oleoresin content was 10% of lycopene as measured by an HPLC method. The process yield (by lycopene) was 92%.

The tomato oleoresin was then used as the raw material for the production of crystalline lycopene. 1.25 kg of the tomato oleoresin was suspended in 5 kg of ethanol, heated to 60° C. and filtered through a 10 μm filter. After solvent removal, 188 g of the lycopene crystals were collected on the filter. The crystals thereby obtained contained 70% lycopene and 30% tomato oil. The process yield (by lycopene) was about 85%.

Example 2

Production of Lycopene Crystals in Accordance with the Present Invention

One ton of ripe tomatoes containing 165 ppm of lycopene (165 mg/kg) were washed and minced.

Tomato peels and seeds were separated from the crushed tomatoes through two sieves. For first step a sieve of 4 mm was used and after that a sieve of 0.8 mm.

After peel and seeds separation, tomato juice was loaded into a vessel which was evacuated using negative pressure for 30 minutes. Afterwards, the tomato juice was heated to 82-86° C. with a heat exchanger and separated into pulp (containing tomato fibers and lycopene) and serum (containing soluble tomato solids) by passing it through a decanter. One ton of the tomato produced 41 kg of wet pulp, with 80% moisture content and a lycopene concentration of 3800 ppm. The process yield by lycopene was 94%.

The wet pulp was used as the raw material for the extraction of lycopene. Ethyl acetate was used as the extraction solvent, the ratio between the ethyl acetate and the tomato pulp being 2.0:1 (w/w). The extraction was performed at 60° C. for 4 hours. The extraction process resulted in about 0.80 kg of tomato oleoresin. Oleoresin content was 15% of lycopene as measured by an HPLC method. The process yield (by lycopene) was 94%.

The tomato oleoresin was then used as the raw material for the production of crystalline lycopene. 0.90 kg of the tomato oleoresin was suspended in 4 kg of ethanol, heated to 60° C. and filtered through a 10 μm filter. After solvent removal, 155 g of the lycopene crystals were collected on the filter. The crystals thereby obtained contained 85% lycopene and 15% tomato oil. The process yield (by lycopene) was 85-87%.

Example 3

Determination of Concentration of Insoluble Material in the Composition of the Present Invention The concentration of methylene chloride-insoluble material in different batches of the composition of the present invention (prepared in accordance with Example 2), as well as in batches of a composition prepared according to a prior art method (as described in Example 1) was determined by means of the following method, which is based on the filtration of the sample solution and weighing the insoluble matter remaining on the filter.

Method:
Weigh accurately about 2.5 g of the sample into a flask, and add methylene chloride (100 ml).
Sonicate the solution for 10 min.
Refrigerate the solution at 5° C. for 30 min.
Filter the sample solution through a 0.8 μm PTFE membrane filter, previously dried and weighed.
Wash with 50 ml methylene chloride at 5° C.
Dry the washed membrane filter at 85° C., cool in desiccators containing dry silica gel and record the weight of the dried filter.

Insoluble matter (%)=((weight of filter after use− weight of filter before use)/weight of the sample)×100.

Example 4

Determination of the Lycopene Concentration in the Tomato Extract

In addition to the assay of methylene chloride-insoluble material, as described above, the concentration of lycopene in the tomato extracts was measured spectrophotometrically. Briefly, 0.02-0.03 g of the tomato extract was accurately weighed into a flask, followed by 10 ml of a BHT solution (2.5 g BHT in 0.51 dichloromethane) and 50 m of dichloromethane. The sample was dissolved by sonication in an ultrasonic bath. 5 ml of this solution was taken into a 100 ml volumetric flask, made up to volume with petroleum ether, and then mixed well. The absorbance of this solution from 550 nm to 350 nm is scanned, using petroleum ether as a reference, in covered glass cuvettes having a 1 cm light path. Three specific absorbance peaks are seen, and the absorbance at approximately 472 nm (the middle peak) is recorded ($A_{472}$).

The concentration of lycopene in the composition (by percentage) is determined using the following formula:

% lycopene=($A_{472}$×Dil×100)/(weight of sample in grams×3,450).

Where $A_{472}$ is the absorbance at 472 nm; Dil is the dilution factor

Example 5

Lycopene and Insoluble Material Concentrations of Compositions of the Present Invention and Prior Art Compositions The percentage of insoluble material and the percentage of lycopene were separately measured (as described hereinabove) in 42 batches of the composition of the present invention (prepared in accordance with Example 2) and in 25 batches of a prior art composition (prepared in accordance with Example 1) having a nominal lycopene concentration of about 70%. The results obtained are summarized in the following tables:

TABLE 1

Lycopene concentration and insoluble material concentration of 48 separate batches of the composition of the present invention

| Batch# | Lycopene concentration (%) | Insoluble material (%) |
|---|---|---|
| 1 | 78.5 | 7.14 |
| 2 | 78.3 | 4.77 |
| 3 | 78.7 | 4.92 |
| 4 | 76.6 | 6.07 |
| 5 | 79.9 | 4.22 |
| 6 | 79.1 | 7.62 |
| 7 | 74.0 | 4.63 |
| 8 | 79.4 | 4.18 |
| 9 | 76.1 | 5.83 |
| 10 | 77.0 | 4.61 |
| 11 | 76.2 | 4.74 |
| 12 | 79.4 | 5.94 |
| 13 | 80.8 | 7.93 |
| 14 | 78.3 | 7.80 |
| 15 | 84.9 | 5.06 |
| 16 | 76.1 | 1.34 |
| 17 | 76.8 | 2.15 |
| 18 | 75.8 | 3.35 |
| 19 | 80.4 | 1.40 |
| 20 | 80.1 | 2.35 |
| 21 | 77.0 | 2.48 |
| 22 | 78.3 | 5.42 |
| 23 | 77.3 | 5.82 |
| 24 | 80.1 | 5.61 |
| 25 | 82.5 | 3.50 |
| 26 | 86.7 | 4.25 |
| 27 | 81.9 | 6.55 |
| 28 | 74.0 | 9.70 |
| 29 | 75.3 | 5.27 |
| 30 | 76.6 | 5.48 |
| 31 | 78.3 | 8.10 |
| 32 | 76.5 | 5.25 |
| 33 | 76.8 | 3.82 |
| 34 | 77.0 | 3.65 |
| 35 | 79.8 | 5.01 |

TABLE 1-continued

Lycopene concentration and insoluble material concentration of 48 separate batches of the composition of the present invention

| Batch# | Lycopene concentration (%) | Insoluble material (%) |
|---|---|---|
| 36 | 76.4 | 5.25 |
| 37 | 78.3 | 9.29 |
| 38 | 78.0 | 6.12 |
| 39 | 75.5 | 5.97 |
| 40 | 76.8 | 3.42 |
| 41 | 78.4 | 5.04 |
| 42 | 75.4 | 4.37 |
| AVERAGE | 78.2 | 5.13 |
| SD | 2.591 | 1.896 |

TABLE 2

Lycopene concentration and insoluble material concentration of 25 separate batches of a prior art composition having a nominal lycopene concentration of about 70%

| Batch# | Lycopene concentration (%) | Insoluble material (%) |
|---|---|---|
| 1 | 63.3 | 18.48 |
| 2 | 54.1 | 14.49 |
| 3 | 71.7 | 15.69 |
| 4 | 75.6 | 16.21 |
| 5 | 73.2 | 14.79 |
| 6 | 71.4 | 14.21 |
| 7 | 72.3 | 14.37 |
| 8 | 72.0 | 15.5 |
| 9 | 74.2 | 16.84 |
| 10 | 75.2 | 10.46 |
| 11 | 71.1 | 12.83 |
| 12 | 78.3 | 11.36 |
| 13 | 74.9 | 13.18 |
| 14 | 78.8 | 11.70 |
| 15 | 71.9 | 15.04 |
| 16 | 71.8 | 17.13 |
| 17 | 69.6 | 19.88 |
| 18 | 75.0 | 13.75 |
| 19 | 75.8 | 12.89 |
| 20 | 77.7 | 12.07 |
| 21 | 76.5 | 12.13 |
| 22 | 76.2 | 12.10 |
| 23 | 74.8 | 11.39 |
| 24 | 70.5 | 10.17 |
| 25 | 75.9 | 11.56 |
| AVERAGE | 72.9 | 13.93 |
| SD | 5.119 | 2.507 |

As will be seen from the results presented in these tables, the presently-claimed composition has an average lycopene concentration of 78.2% (w/w)±2.59 and an average insoluble material concentration of 5.13% (w/w)±1.896. In contrast, the prior art composition has a lower average lycopene concentration—72.9% (w/w)±5.12—and a much higher average insoluble material concentration: 13.93% (w/w)±2.507.

Example 6

Formulation Analysis

The following three formulation examples clearly demonstrate the unexpected relationship of the concentration of insoluble material in the tomato-derived lycopene composition and the color characteristics of that composition. In these examples, the L*a*b* color characteristics of a 10 ppm aqueous solution of each formulation were determined using a Hunter Lab ColorQuest XE colorimeter, operating in transmission mode. Four separate batches of each formulation were subjected to this analysis. The key L*a*b* color parameters may be briefly summarized as follows:
i) The L parameter is a measure of the lightness of the sample;
ii) The a parameter provides a measure of redness (when said parameter has a positive value) and greenness (when said parameter has a negative value);
iii) The b parameter provides a measure of yellowness (positive values) and blueness (negative values).

The C parameter (chroma or color intensity) and the h parameter (the hue angle), are calculated from the a and b values.

Formulations considered as having desirable color properties were those achieving the following L*a*b* target values:
a value: 25;
b value: 11.25-14.5;
b/a=0.45-0.55;
C value: 27.5-32.5;
h value: 24.2-27.0.

Example 7

Color Formulation with Lycopene Crystals Containing 5% Insoluble Material

Materials:
10 kg crystalline lycopene (comprising 5.1% insoluble material, as measured by the method described hereinabove in Example 3)
20 kg sucrose ester
15 kg sunflower de-oiled lecithin
300 g ascorbic acid
150 kg mixture of glycerol and water
Process:
All ingredients were mixed using high sheer mixer to homogenous suspension. Using a ball mill (milling chamber was 5l), the lycopene crystals were reduced from 50-100 μm to 50-400 nm. The milling time was between 12-15 hrs. The L*a*b* color characteristics of a 10 ppm water solution of the formulation were analyzed as explained hereinabove, and found to be: L value=42-47; a value=25-28; b value=11.5-14.

Stability:
The stability of the formulation was evaluated in a beverage. Two beverage systems were used:
First beverage system: sugar syrup 11° Bx, pH=3.0, ascorbic acid 200 ppm, lycopene 10 ppm;
Second beverage system: 5% fruit, 10° Bx and pH=3.0-3.2, water soluble flavor, ascorbic acid 200 ppm, lycopene content 5 ppm.

The fruit compound with color was homogenized, at a pressure of 150 Bar. Both beverages were pasteurized at 90-94° C. for 30 sec. For the purpose of stability testing, the beverages were kept under luminescent light at room temperature for 6 months. Control beverages were kept at 4° C. in a refrigerator. Each month, the colored beverages were analyzed with respect to the following parameters: (1) the L, a and b colorimetric values, (2) the appearance of a ring and (3) the presence of a precipitate.

The results obtained (no significant change in the L*a*b* parameters and no ring formation or precipitate) indicate that both beverages (colored with the lycopene composition of the present invention) were entirely stable over the course of the 6 month test period.

Example 8

Color Formulation with Lycopene Crystals Containing 7-9% Insoluble Material

Materials:
10 kg crystalline lycopene (7.5% insoluble material, as measured by the method described in Example 3, hereinabove).
20 kg sucrose ester
15 kg sunflower de-oiled lecithin
300 g ascorbic acid
150 kg mixture of glycerol and water
Process:
All ingredients were mixed using high sheer mixer to homogenous suspension. Using a ball mill (having a 5l milling chamber), the lycopene crystals were reduced in size from 50-100 μm to 50-400 nm. The milling time was approximately 20-22 hrs. The color characteristics were measured as explained hereinabove, and were found to be: L value=42-47; a value=25-28; b value 11.5-14. It will be noted that although a longer grinding time was needed in order to achieve the same size reduction as achieved in Example 7 (which had a lower insoluble material concentration), the color parameters of these two formulations of the present invention were the same.

The stability of the prepared formulation was evaluated in the following two beverage systems:
First beverage system—sugar syrup 11° Bx, pH=3.0, ascorbic acid 200 ppm, lycopene 10 ppm;
Second beverage system—5% fruit, 10° Bx and pH=3.0-3.2, water soluble flavor, ascorbic acid 200 ppm, lycopene content 5 ppm. Fruit compound with color was homogenized at a pressure of 150 Bar. Both beverages were pasteurized at 90-94° C. for 30 sec. For the duration of the stability testing, the beverages were kept under luminescent light at room temperature for 6 months. Control beverages were kept at 4° C. in a refrigerator. Each month, the colored beverages were analyzed with respect to the following parameters: (1) the L, a and b colorimetric values, (2) the appearance of a ring and (3) the presence of a precipitate.

The results obtained (no significant change in the L*a*b* parameters and no ring formation or precipitate) indicate that both beverages (colored with the lycopene composition of the present invention) were entirely stable over the course of the 6 month test period.

Example 9

Color Formulation with Lycopene Crystals Containing 15% Insoluble Material (Comparative)

Materials:
10 kg crystalline lycopene (15.2% insoluble material, as measured by the method described in Example 3, hereinabove)
20 kg sucrose ester
15 kg sunflower de-oiled lecithin
300 g ascorbic acid
150 kg mixture of glycerol and water
All the ingredients were mixed using a high sheer mixer to a homogenous suspension. Using a ball mill (with a 5l milling chamber), the lycopene crystals were reduced in size from 50-100 μm to 50-400 nm. The milling time was approximately 27-48 hr.

The color characteristics of the lycopene composition were measured as explained hereinabove, and were found to be: L value=40-47; a value=20-23; b value 14-19. It will be noted that although a longer grinding time was used, it proved impossible to obtain the desired color intensity and hue with this composition having a high concentration of insoluble material.

The stability of the prepared formulation was evaluated in two different beverage systems:

First beverage system—sugar syrup 11° Bx, pH=3.0, ascorbic acid 200 ppm, lycopene 10 ppm;

Second beverage system—5% fruit, 10° Bx and pH=3.0-3.2, water soluble flavor, ascorbic acid 200 ppm, lycopene content 5 ppm. Fruit compound with color was homogenized, at a pressure of 150 Bar. Both beverages were pasteurized at 90-94° C. for 30 sec. For the purpose of stability testing, beverages were kept under luminescent light at room temperature for 6 month. Control beverages were kept at 4° C. in a refrigerator. Each month, the colored beverages were analyzed with respect to the following parameters: (1) the L, a and b colorimetric values, (2) the appearance of a ring and (3) the presence of a precipitate.

The results obtained (ring formation) indicate that after only 1-2 months, there was a loss of stability in the first beverage system. Also, the color intensity was much lower with this formulation (both beverage systems) than with the formulations containing less than 10% insoluble material (Formulation Examples 7 and 8, above).

The color value results obtained with the two different formulations of the present invention (5% and 7-9% insoluble material; Formulation Examples 7 and 8) and the prior art formulation (15% insoluble material), are summarized in the following table:

| Insoluble material | L | a | b | b/a | C | Hue | Milling time |
|---|---|---|---|---|---|---|---|
| 5% (present invention) | 42-47 | 25-28 | 11.5-14 | 0.45-0.55 | 27.5-32.5 | 24.2-27.0 | 12-15 hr |
| 7-9% (present invention) | 42-47 | 25-28 | 11.5-14 | 0.45-0.55 | 27.5-32.5 | 24.2-27.0 | 20-22 hr |
| 15% (comparative) | 40-47 | 20-23 | 14-19 | 0.7-0.82 | 24.4-29 | 35-40 | 27-48 hr |

It may be seen from these results that the desired a values (25; as explained hereinabove) were obtained only with the two formulations comprising less than 10% insoluble material. When the prior art formulation containing 15% insoluble material was tested, the a value was less than the target value. Similarly, only the two test formulations having lower than 10% insoluble material were found to have a/b values within the target range (0.45-0.55). Finally, both the color intensity (C) and hue (h) values for the two formulations of the present invention were similarly within the desired range, while the prior art composition had values which deviated significantly from the target values.

We conclude that lycopene compositions having less than 10% insoluble material have unexpectedly superior color properties, when compared with compositions having greater than 10% insoluble content. It was also found that in the case of compositions having less than 10% insoluble material, the milling time required in order to achieve that desired lycopene crystal size and color properties decreases as the concentration of said insoluble material decreases.

The invention claimed is:

1. A tomato-derived composition comprising crystals comprising tomato oil, lycopene, and methylene chloride-insoluble material, wherein a concentration of lycopene in the crystals is at least 70% (w/w), a concentration of methylene chloride-insoluble material in the crystals is 10% (w/w) or less, and a size of said crystals comprising tomato oil, lycopene, and methylene chloride-insoluble material is less than 1 micron, wherein the crystals are prepared from crystalizing lycopene, tomato oil, and methylene chloride-insoluble material from a tomato oleoresin obtained from crushed and sieved tomato material having a particle size not greater than 1.5 mm.

2. The composition according to claim 1, wherein the concentration of methylene chloride-insoluble material is less than 9% (w/w).

3. The composition according to claim 2, wherein the concentration of methylene chloride-insoluble material is less than 7% (w/w).

4. The composition according to claim 3, wherein concentration of methylene chloride-insoluble material is about 5% (w/w).

5. The composition according to claim 1, wherein the size of the crystals comprising tomato oil, lycopene, and methylene chloride-insoluble material is in the range of 50-500 nm.

6. The composition according to claim 1, wherein the tomato-derived composition has an 'a' color parameter that is greater than 25.

7. The composition according to claim 1, wherein the tomato-derived composition has a 'b' color parameter that is in a range of 11.25-14.5.

8. The composition according to claim 1, wherein the tomato-derived composition has a ratio of a 'b' color parameter to 'a' color parameter that is in a range of 0.45-0.55.

9. The composition according to claim 1, wherein the tomato-derived composition has a 'C' color parameter that is in a range of 27.5-32.5.

10. The composition according to claim 1, wherein the tomato-derived composition has a 'h' color parameter is in a range of 24.2-27.0.

11. A food, beverage, nutraceutical, or cosmetic product comprising the composition according to claim 1.

12. A process for preparing a tomato-derived composition comprising crystals comprising tomato oil, lycopene, and methylene chloride-insoluble material, wherein a concentration of lycopene in the crystals is at least 70% (w/w), a concentration of methylene chloride-insoluble material in the crystals is 10% (w/w) or less, and a size of said crystals comprising tomato oil, lycopene, and methylene chloride-insoluble material is less than 1 micron, the method comprising crushing and sieving tomatoes to provide crushed and sieved tomato material having a particle size not greater than 1.5 mm, separating pulp from the crushed and sieved tomato material, wherein said pulp has a lycopene concentration of at least 2000 ppm, extracting said pulp with a solvent to obtain a tomato oleoresin, crystallizing lycopene, tomato oil, and methylene chloride-insoluble material from the tomato oleoresin, separating the crystals from the tomato oleoresin, placing said crystals in a liquid medium that does not dissolve lycopene and grinding said crystals to an average particle size of less than 1 micron.

13. The process according to claim 12, wherein the composition produced thereby has one or more color parameters selected from the group consisting of: a value greater than 25; b value: 11.25-14.5; b/a=0.45-0.55; C value: 27.5-32.5; and h value: 24.2-27.0.

14. The composition according to claim 1, wherein the tomato oleoresin is prepared by 1) separating pulp from the crushed and sieved tomato material, wherein said pulp has a lycopene concentration of at least 2000 ppm, and 2) extracting said pulp with a solvent to obtain the tomato oleoresin, wherein the solvent is ethyl acetate.

15. The composition according to claim 1, wherein the crystals are prepared from crystalizing lycopene, tomato oil, and methylene chloride-insoluble material from the tomato oleoresin obtained from crushed and sieved tomato material having a particle size not greater than 0.8 mm.

* * * * *